United States Patent
Shastri et al.

(10) Patent No.: US 9,840,593 B2
(45) Date of Patent: Dec. 12, 2017

(54) PHASE SEGREGATED BLOCK COPOLYMERS WITH TUNABLE PROPERTIES

(71) Applicant: ALBERT-LUDWIGS-UNIVERSITÄT FREIBURG, Freiburg (DE)

(72) Inventors: V. Prasad Shastri, Freiburg (DE); Maziar Matloubigharagozloo, Freiburg (DE)

(73) Assignee: ALBERT-LUDWIGS-UNIVERSITÄT FREIBURG, Freiburg (DE)

( * ) Notice: Subject to any disclaimer, the term of this patent is extended or adjusted under 35 U.S.C. 154(b) by 0 days.

(21) Appl. No.: 15/134,739

(22) Filed: Apr. 21, 2016

(65) Prior Publication Data
US 2016/0244570 A1 Aug. 25, 2016

(30) Foreign Application Priority Data
Feb. 24, 2015 (EP) ..................................... 15156263

(51) Int. Cl.
| C08G 77/00 | (2006.01) |
| C08G 77/445 | (2006.01) |
| A61L 31/06 | (2006.01) |
| A61L 31/14 | (2006.01) |
| A61L 27/50 | (2006.01) |
| A61L 29/06 | (2006.01) |
| C08G 18/61 | (2006.01) |
| C08G 18/42 | (2006.01) |
| C08G 18/73 | (2006.01) |
| A61L 27/18 | (2006.01) |
| A61L 29/14 | (2006.01) |

(52) U.S. Cl.
CPC ............ *C08G 77/445* (2013.01); *A61L 27/18* (2013.01); *A61L 27/50* (2013.01); *A61L 29/06* (2013.01); *A61L 29/14* (2013.01); *A61L 31/06* (2013.01); *A61L 31/14* (2013.01); *C08G 18/428* (2013.01); *C08G 18/61* (2013.01); *C08G 18/73* (2013.01); *A61L 2400/16* (2013.01); *C08G 2280/00* (2013.01)

(58) Field of Classification Search
None
See application file for complete search history.

(56) References Cited

U.S. PATENT DOCUMENTS

| 5,202,413 | A  | * | 4/1993 | Spinu | C08G 18/428 525/415 |
| 6,281,262 | B1 | * | 8/2001 | Shikinami | A61B 17/846 264/230 |
| 7,244,444 | B2 | * | 7/2007 | Bates | A61F 2/06 424/400 |
| 2005/0010275 | A1 | * | 1/2005 | Sahatjian | A61F 2/88 623/1.11 |
| 2005/0216074 | A1 | * | 9/2005 | Sahatjian | A61F 2/88 623/1.11 |
| 2005/0245719 | A1 | * | 11/2005 | Mather | C08G 18/3893 528/60 |
| 2006/0041089 | A1 | * | 2/2006 | Mather | C08F 246/00 526/147 |
| 2007/0282435 | A1 | * | 12/2007 | Wang | A61L 27/18 623/1.38 |
| 2009/0004243 | A1 | * | 1/2009 | Pacetti | A61L 29/041 424/426 |
| 2009/0035350 | A1 |   | 2/2009 | Stankus et al. | |

FOREIGN PATENT DOCUMENTS

| AU | 630925 B2 | 11/1992 |
| WO | WO 94/19384 A1 | 9/1994 |
| WO | WO 99/42147 A1 | 8/1999 |
| WO | WO 2006/115799 | 11/2006 |

OTHER PUBLICATIONS

European Search Report and Opinion received in connection with application No. EP 15156263; dated Aug. 12, 2015.

* cited by examiner

*Primary Examiner* — Robert S Loewe
(74) *Attorney, Agent, or Firm* — The Marbury Law Group, PLLC

(57) ABSTRACT

Phase segregated block-copolymer based on repeating structural elements represented by formula I (I)

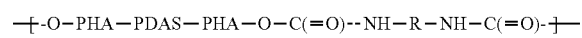

wherein PHA represents at least one block based on one or more α-hydroxy acids, PDAS represents a central block based on a dialkylsiloxane,
the PDAS block has a weight average molecular weight in the range of from 4000 to 10000,
the blocks PHA have a weight average molecular weight in the range of from 2000 to 10 000,
the phase segregated block copolymer has a weight average molecular weight of from 40 000 to 120 000.

18 Claims, No Drawings

PHASE SEGREGATED BLOCK COPOLYMERS WITH TUNABLE PROPERTIES

CLAIM FOR PRIORITY

This application claims priority to European Patent Application No. EP 15156263.4, filed Feb. 24, 2015, of the same title, the disclosure of which is incorporated herein in its entirety.

The present invention relates to phase segregated block copolymers comprising blocks with different transition temperatures (hard and soft segments) which are linked through urethane linkages.

Phase segregated block copolymers with hard and soft segments are an interesting group of polymers which have found increasing attention in the recent past. In particular so called shape memory polymers of this type may be mentioned in this regard.

Shape memory, in the context of the present invention, is to be understood as the ability of a material to remember and recover its original shape after it has been subjected to a deformation, which deformation may be caused by e.g. mechanical stress. This deformation can be recovered by introducing heat. This phenomenon is generally based on structural phase transformations in the material.

Shape memory materials based on metallic materials have been known for a while but for certain applications metallic materials may lead to problems and are thus undesirable (especially in biomaterials that have direct contact to human body tissues).

Shape memory polymers have also been described in the literature.

WO 99/42147 describes biodegradable shape memory polymer compositions comprising at least one hard segment having a transition temperature between −40 and 270° C. and at least one soft segment which has a transition temperature which is at least 10° C. lower than that of the hard segment, which soft segment is linked to at least one hard segment wherein at least one hard or soft segment includes a biodegradable region or wherein at least one of the hard segments is linked to at least one of the soft segments through a biodegradable linkage. The term transition temperature denotes the melting point in case of a crystalline segment or the glass transition temperature in case of an amorphous segment. Preferably, at least one of the hard and soft segments is a thermoplastic polymer and the hard segment preferably comprises cyclic moieties.

Polyhydroxy acids are mentioned amongst the group of preferred polymers with a biodegradable region and polylactides are mentioned as degradable polymer segments on page 11, line 14.

Gonsalves et al., J. Pol. Sci. Part A. Pol. Chem. Vol 34, 2737-2742 (1996) disclose the copolymer synthesis of poly (L-lactide-b-DMS-L-lactide) polymers via the ring opening polymerization of L-lactide in the presence of hydroxypropyl-terminated poly dimethyl siloxane (PDMS).

Djonlagic et al., J. Appl. Pol. Sci. Vol. 122, Issue 4, pp 2715-2730 (2011) describe novel polyurethane copolymers derived from a diisocyanate, butane diol and a hydroxy terminated PCL-PDMS-PCL oligomer which are synthesized by a two step polyaddition reaction.

Cooper et al., J. Pol. Sci. Pol. Phys. Ed. 23, 2319-2338 (1985) describe polyurethane block polymers obtained through the reaction of hydroxyl-terminated PDMS soft segments with a molecular weight of 2000 and 4,4' methylene diphenylene diisocyanate.

WO 2006/115799 discloses a biodegradable shape memory polymer comprising the reaction product of a polyol A, a dihydroxyl terminated oligosilsesquioxane B (also referred to as POSS) and a diisocyanate, wherein the polyol is semicrystalline and selected from the group of biodegradable and non-biodegradable polyols or mixtures thereof.

US2009/035350 discloses a composition comprising a biodegradable shape-memory polymer comprising at least two segments with different glass transition or melting temperatures wherein one segment is made from at least one diisocyanate and at least one diol and the second segment is derived from a polymer comprising at least one hydroxyl, amino or thiol end group.

P. Boehm in his PhD Thesis entitled "Functional silicones and Silicone-Containing Block Copolymers (Johannes Gutenberg University of Mainz, Germany) describes in chapter 2.3. starting on page 79 AB and ABA block copolymers based on poly(lactide) and poly(dimethylsiloxane) as strongly phase segregated systems. Synthesis of these polymers was carried out using hydroxyl end-functionalized poly (dimethyl siloxane)s, prepared via anionic or cationic ring-opening polymerization, as a macro initiator for the ring-opening polymerization of the dilactide.

WO 2009/20,797 discloses compositions comprising a biodegradable copolymer comprising at least two segments A and B wherein the A segment has a transition temperature in the range from about 50° C. to about 300° C. and is made from at least one diisocyanate and at least one dial, diamine or dithiol chain extender wherein the B segment has a transition temperature at least 20° C. below the transition temperature of segment A, which segment A is derived from a polymer containing at least one hydroxyl, amino or thiol end group. The compositions are said to be particularly useful for implantable devices like e.g. stents or the like.

While the products which have been described in the prior art cited above show an interesting property spectrum, there still exists an ongoing need for further phase segregated polymeric systems with tunable properties.

It was thus an object of the present invention to provide phase segregated polymers which have an interesting property spectrum and the properties of which are tunable to the desired application through modifications in their composition.

This objective has been achieved with the phase segregated copolymers in accordance with claim 1.

Preferred embodiments of the present invention are set forth in the dependent claims and in the detailed specification hereinafter.

The phase segregated block copolymers in accordance with the present invention are based on structural elements represented by formula (I)

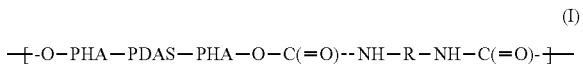

(I)

wherein PHA represents at least one block based on one or more α-hydroxy acids,

PDAS represents a central block based on a dialkylsiloxane, the PDAS block has a weight average molecular weight in the range of from 4000 to 10000, the blocks PHA have a weight average molecular weight in the range of from 1500 to 10 000, and the phase segregated block copolymer has a weight average molecular weight of from 40 000 to 120 000

The phase segregated block-copolymers in accordance with the present invention comprise blocks (hereinafter referred to as PHA) based on one or more α-hydroxy acids (HA).

α-hydroxy acids (HA) are a class of compounds comprising a carboxyl group (COOH) and a hydroxyl group on adjacent carbon atoms, i.e. they follow the general formula

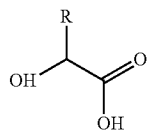

wherein R may be a linear, branched, or cyclic aliphatic group, an aryl group comprising 6 to 30 carbon atoms which may comprise a fused ring, or an alkylaryl group having 7 to 40 carbon atoms and wherein the hydrogen atoms at the carbon atoms of R may be replaced with other groups.

For the purpose of the present invention PHA blocks which are biodegradable are especially preferred.

Aliphatic polyesters derived from α-hydroxy acids have been widely investigated as they often show an interesting degree of biodegradability.

α-hydroxy acids, the polymers of which are biodegradable, are often derived from food products, such as glycolic acid (from sugar cane), lactic acid (from sour milk or fermentation of carbohydrates such as sugar cane, beet and corn), malic acid (from apples), citric acid (from citrus fruits) and tartaric acid (from grape wine).

Another group of biocompatible (i.e. biodegradable) polyesters may be derived from α-hydroxy acids which have been obtained through diazotation of α-amino acids in accordance with the following general reaction scheme

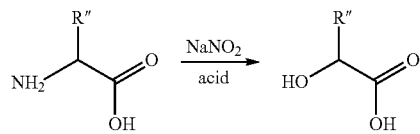

α-amino acids are naturally occurring in a wide variety and can be synthesized by known methods so that the α-hydroxy acids derived therefrom are also quite readily available. Katzhendler et al., Polymers 2010, 2, 418-439 (2010) describe the hydrolytic degradation behaviour of biocompatible polyesters derived from a number of α-hydroxy acids obtained from α-amino acids, including Leucin, Isoleucin, Phenylalanine and Valin, either as homopolymers or as copolymers with other α-hydroxy acids including e.g. lactic acid and glycolic acid or hydroxyhexanoic acid.

The data shown by Katzhendler also include glass transition temperatures for the homo and copolymers and the data show that the glass transition temperature can be tuned by appropriately selecting the proportions of the various α-hydroxy acids. Thus, e.g. the glass transition temperature of PLA which is around 50-60° C. can be lowered by including units derived from the other α-hydroxy acids.

Preferred α-hydroxy acids for the PHA blocks in the phase segregated block copolymers in accordance with the present invention are malic acid, glycolic acid and lactic acid, in particular lactic acid and glycolic acid or combinations thereof in the form of block or random copolymers.

The detailed description refers to these α-hydroxy acids as representatives but in principle any α-hydroxy acid which can be converted to biodegradable PHA blocks, may be used in accordance with the present invention.

The PHA blocks may be homopolymers of one α-hydroxy acid, such as polyglycolic acid (PGA) or polylactic acid (PLA) or they may comprise units derived from more than one α-hydroxy acid, such as e.g. poly(lactide-co-glycolide) where the units derived from the different α-hydroxy acids may be present in block or random distribution in the PHA block.

Accordingly PHA may denote PLA blocks, PGA blocks or blocks having constituting elements based on PLA-PGA combinations. The blocks may comprise one or more than one block based on PLA and PGA, such as e.g. three-block copolymers PGA-PLA-PGA or PLA-PGA-PLA to give only two examples.

The weight average molecular weight of the PHA blocks in the phase segregated block copolymers in accordance with the present invention is in the range of from 1500 to 10 000, preferably of from 2000 to 7000 and most preferably in the range of from 2200 to 5500.

The weight average molecular weight $M_w$ of a polymer takes into account the molecular weight of individual chains in determining the contribution to the molecular weight average. The higher the molecular weight of an individual chain in the ensemble, the higher the contribution thereof to $M_w$. Accordingly, $M_w$ is determined by methods that are sensitive to the molecular size. A $M_w$ of 5000 means that 50% of the total weight is comprised of molecules of individual molecular weights of less than 5000 and 50% of the total weight is comprised of molecules having an individual molecular weight of more than 5000.

The weight average molecular weight as referred to in the context of the present invention is determined by gel permeation chromatography using a GPC 1200 System with isocratic pump, preparative auto sampler, varialbie wavelength UV-detector and refractive index detector. Calibration was made with Ready Cal-Kit High (Polymer Standards Services) and PS-H Tri pack (Agilent technologies (both calibration kits using narrow molecular weight distribution polystyrene. The columns used were SDV Precolumn and SDV 100 Å, SDV 1000 Å and SDV 10 000 Å at a temperature in the range of from 21.5 to 22.5° C. and a flow rate of 1 ml/min. Measurement time was 50 minutes. The data were evaluated and analyzed with the PSS WinGPC Unity 7.21 software.

The phase segregated block-copolymer in accordance with the present invention comprise polydialkylsiloxane blocks (hereinafter referred to as PDAS, which blocks have a weight average molecular weight in the range of from 4000 to 10 000, preferably of from 4500 to 8500 and even more preferably of form 5000 to 7500 which are bound at their terminal ends to PHA blocks so that a structural element PHA-PDAS-PHA results.

A siloxane is a functional group in organosilicon chemistry with the Si—O—Si-linkage. The word siloxane is derived from the words silicon, oxygen and alkane. Siloxane materials may be composed of several types of so called siloxide groups, depending on the number of Si—O bonds: M-units represented by general structural element $R_3SiO_{0.5}$, D-units by the general structural element $R_2SiO$ and T-units represented by the general structural element $RSiO_{1.5}$.

Siloxane functional groups form the backbone of the silicones.

Polydialkylsiloxanes may be represented by the following general formula

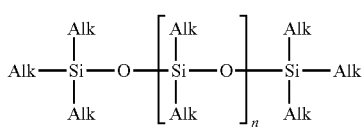

wherein Alk, which may be the same or different at each occurence, represents a linear, branched or cyclic alkyl group.

In accordance with the above nomenclature polydialkylsiloxanes may be denoted as M-$D_n$-M.

Preferred alkyl groups are linear or branched alkyl groups having 1 to 12, preferably 1 to 8 and more preferably 1 to 4 carbon atoms.

The best known example of polydialkylsiloxanes is polydimethylsiloxane (where Alk is a methyl group, hereinafter referred to as PDMS), which is also the most preferred polydialkylsiloxane in accordance with the present invention.

The phase segregated block copolymers in accordance with the present invention are preferably obtained by a reaction sequence comprising several steps.

In the first step a hydroxyl terminated polydialkylsiloxane HO-PDAS-OH having a molecular weight as disclosed above is reacted with a α-hydroxy acid or a mixture of α-hydroxy acids or derivatives thereof or a hydroxyl terminated α-hydroxy acid polymer HO-PHA-OH to obtain at the end a hydroxyl terminated block copolymer HO-PHA-PDAS-PHA-OH.

Hydroxyl terminated polydialkylsiloxanes, e.g. hydroxyl terminated PDMS with molecular weights in the range required are either commercially available for various sources (e.g. Sigma Aldrich) or may be obtained in accordance with processes known to the skilled person so that no further details need to be given here.

The hydroxyl terminated block copolymer obtained in the first step is thereafter reacted with a diisocyanate, optionally in the presence of chain extenders to obtain the final product comprising the urethane linkage. The second step principally corresponds to a classical polyurethane synthesis reaction of a polyol with a diisocyanate (or a polyisocyanate with more than two isocyanate groups) and has been described in many literature references.

Suitable isocyanates are the isocyanates commonly used for polyurethane synthesis, i.e. di- or multifunctional isocyanates having two or more than two —NCO groups per molecule. The isocyanates may be aliphatic, cycloaliphatic, polycyclic or aromatic in nature. Just by way of example, toluylene diisocyanate (TDI), methylene diisocyanate (MDI), xylene diisocyanate (XDI), meta-tetramethylxylylene diisocyanate (TMXDI), naphthalene-1,5-diisocyanate (NDI), p-phenylene-diisocyanate (PPDI), 3,3'-dimethyldiphenyl-4,4'-diisocyanate (DDDI), 1,6-hexamethylene diisocyanate (HMDI or HDI), 2,2,4-trimehtylhexamethylene diisocyanate (TMDI), isophorone diisocyanate (IPDI), 4,4'-dicyclohexylmethane diisocyanate ($H_{12}$MDI), norbornane diisocyanate (NDI) or 4,4'-dibenzyl diisocyanate (DBDI) may be mentioned here. In principle, however, the selection of the diisocyanate is not subject to particular limitations and the skilled person will select a suitable diisocyanate based on his or her professional experience and adapted to the specific situation. Suitable diisocyanates are commercially available from a number of sources and the skilled person is aware of suitable methods for their manufacture so that no further details need to be given here.

In accordance with a preferred embodiment of the present invention, in the first step a hydroxyl-terminated polydimethyl siloxane is reacted with lactide (or a mixture of lactide and glycolide) to obtain a triblock copolymer having a central block derived from polydimethylsiloxane sandwiched between two PHA blocks which have terminal hydroxyl groups. The reaction is a so called ring opening polymerization (ROP) which may be summarized by the following general reaction scheme (shown for lactide):

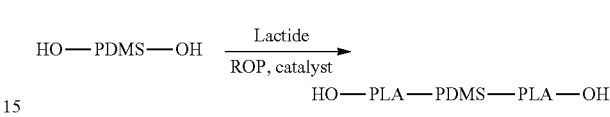

Lactide, the cyclic diester of lactic acid, has the following structure

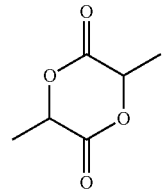

and glycolide is the respective compound wherein the methyl groups are replaced by hydrogen atoms.

The ring opening polymerization of lactides with hydroxyl terminated polydimethylsiloxanes in the presence of a tin catalyst has been described in the literature, e.g. by Gonsalves et al. J. Pol Science Part A: Polymer Chemistry Vol. 34, 2737 (1996). SnOct$_2$ (stannous octoate), the hydroxyl terminated PDMS and the lactide were reacted in a sealed tube in a heated oil bath to obtain the desired products. By varying the molar ratio of lactide and PDMS block copolymers with different percentages of PDMS and PLA units were obtained.

The content of the PHA segments in the PHA-PDAS-PHA copolymers is not particularly critical, but in general is in the range of from 20 to 80 wt %, preferably in the range of from 33 to 75% by weight and most preferably in the range of from 40 to 70% by weight, based on the entire weight of the PHA-PDAS-PHA polymer.

Paul Boehm in his PhD thesis at the University of Mainz, entitled "Functional silicones and silicone containing block copolymers" starting on page 78 discloses the preparation of ABA block copolymers consisting of PDMS and PLA segments by using hydroxyl end-functionalized PDMS for cationic or anionic ring opening polymerization of dilactide to obtain copolymers with various block-length ratios which may be steered through the molar ratio of the reactants. The bis-hydroxy functionalized PDMS was mixed together with the lactide and dissolved in anhydrous methylene chloride. The polymerization was started by the addition of 1 mol % of DBU (with respect to the amount of lactide) which was added through a syringe. The reaction was quenched after 20 min at ambient temperature by the addition of benzoic acid and the prodcut mixture was purified to obtain the desired block copolymers.

The foregoing literature references are only two examples showing the reaction of hydroxyl terminated PDMS with lactides and the skilled person will select the most appropriate specific reaction conditions depending on the desired molecular weight of the product.

In certain cases, the use of a tin organic compound as catalyst has proved to be advantageous and thus represents a preferred embodiment of the present invention. The reaction temperature with Sn catalysts is generally in the range of from 60 to 120° C., preferably in the range of from 70 to 100° C. The skilled person will choose the molar ratio of PDMS and lactide to achieve a desired molecular weight of the product as is well known for this kind of reaction. No further details need to be given here.

Block copolymers based on other polydialkylsiloxanes and/or other α-hydroxy acids may be obtained in an analogous manner by using the appropriate starting materials.

In accordance with a further embodiment of the present invention, fluorinated diols may be used as co-monomers in the synthesis of the PDAS blocks used as starting material, in the synthesis of the intermediate products or together with the di- or polyisocyanate in the final step as chain extender. The amount of such co-monomers is not subject to particular limitations but amounts of 10 mol %, preferably 5 mol % or less, based on the entire weight of the diols respectively di- or polyisocyanates have shown to be useful. Due to the polar nature of the fluorine atoms and the low surface energy of fluorinated polymers the oligomeric segments comprising such fluorinated components migrate and may be segmented on the surface which introduces anti-fouling and non-coagulant properties to the surface, which is in particular advantageous for materials in contact with blood like e.g. stents.

Just by way of example for fluorinated co-monomers or chain extenders fluorinated dihydroxy polyethers (often referred to as FHPE) which are known to the skilled person and which are commercially available from a number of sources. Just by way of example, fluorinated polyether compounds of the general formula T'-Q'$_y$-R$_f$-Q-T$_k$, wherein R$_f$ is a monovalent or divalent polyfluoropolyether group, Q and Q' are independently a chemical bond or a divalent organic linking group and T and T' are hydroxyl groups may be mentioned here. Two exemplary compounds of this type are reproduced below:

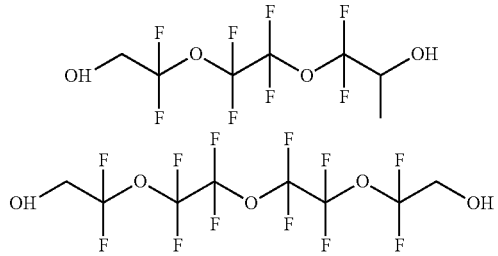

The skilled person is ware of other suitable fluorinated polyether compounds and will select the appropriate compound based on the specific application situation.

As is apparent from the foregoing description, by choosing the appropriate reaction conditions and the molar ratio of the reactants, block copolymers of various compositions may be obtained.

If more than one α-hydroxy acid is used as reactant, PHA blocks comprising more than one HA repeating unit may be obtained and if different α-hydroxy acids are reacted sequentially, PHA blocks may be obtained which themselves comprise blocks of different HA units, i.e. differing from a random distribution which is obtained when using a mixture. The skilled person will use the molar ratio of the reactants as well as the simultaneous or sequential addition for steering the synthesis.

The hydroxyl terminated block copolymers obtained in the first reaction step are then reacted with a polyisocyanate. The hydroxyl-terminated block copolymer serves as a "polyol" in the reaction, which is a classical method for the synthesis of polyurethanes. The skilled person is aware of the suitable reaction conditions and will carry out the reaction in an appropriate manner adapted to the desired application and to achieve the weight average molecular weight in the range of from 40,000 to 120,000, preferably of from 40,000 to 100,000 and even more preferably in the range of from 50,000 to 90,000.

The choice of isocyanate is not particularly critical and in principle any type of isocyanate may be used. As biodegradability or biocompatibility is a preferred property of the products, aliphatic isocyanates are generally preferred, however and methylene diisocyanate or hexamethylene diisocyanate may be mentioned as two examples.

The reaction conditions for the reaction of the polyisocyanate with the hydroxyl terminated block copolymer in the first step are not particularly critical and may be selected depending on the polyisocyanate used.

The molecular weight of the final product can be controlled by choosing the appropriate molar ratio of polyisocyanate and block copolymer as is known to a skilled person for the molecular weight control in a step-growth addition polymerization.

From the foregoing it is apparent that the phase segregated block copolymers in accordance with the present invention are characterized by structural elements of general formula I.

Just by way of example the following scheme shows the synthesis of two types of phase segregated block copolymers in accordance with the present invention with polydimethylsiloxane as PDAS element and lactide as PHA element.

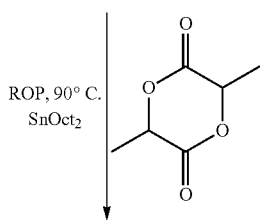

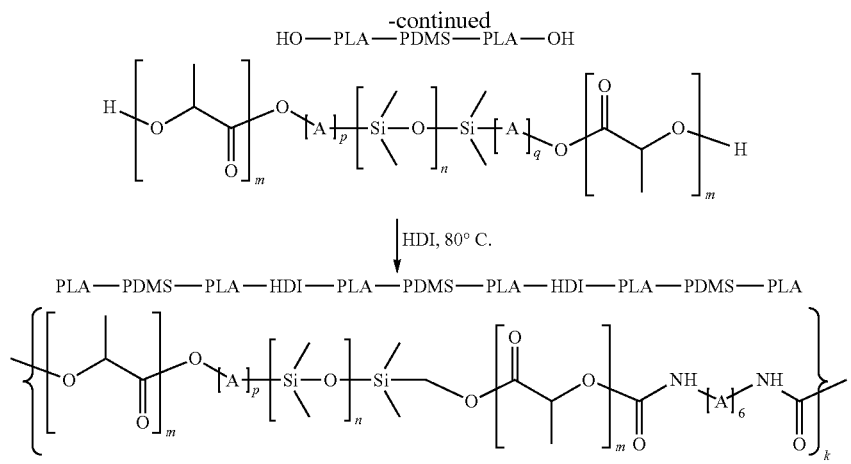

It is readily apparent that by using mixtures of lactide and glycolide or sequential reaction of lactide and glycolide in the first step. the structure of the PHA block may be modified.

Phase segregated block copolymers obtained from the reaction of PDMS and lactice and/or glycolide in the first step and subsequent reaction with a polyisocyanate are the most preferred block copolymers of the present invention.

The variables m and n in the scheme above characterize the block length of the PHA and the PDAS block and are selected so as to fulfill the molecular weight requirements described above.

A and A', independent of one another. represent $SiR_2$ or $CR_2$ wherein R is a hydrogen atom or an alkyl group with 1 to 8 carbon atoms.

The parameters p and q represent the number of silylene or alkylene groups if the hydroxyl functionalized PDAS is terminated by hydroxyalkyl groups or hydroxysilyl groups. In case of OH-end groups as such, p and q are 0.

In accordance with a preferred embodiment, the phase segregated block-copolymers in accordance with the present invention have a polydispersity index (PDI) of less than 1.8, preferably of less than 1.7 and even more preferably of less than 1.6. The PDI is obtained by dividing weight average molecular weight by number average molecular weight a given product.

As mentioned before, the phase segregated block copolymers in accordance with the present invention are preferably biodegradable or biocompatible. For the purpose of the present invention, biodegradable denotes a substance, which is chemically dissoluted, e.g. degraded or broken down, by the action of bacteria or by other biological means. In general, respective materials degrade by hydrolysis, by exposure to water or enzymes under physiological conditions, by surface erosion, bulk erosion or a combination thereof. The degradation may occur at different rates, depending on the conditions of the environment such as temperature, oxygen content, water content and the like. In the course of the biodegradation the polymeric molecules are broken down to small fragments. Generally, the breakdown of the polymer occurs to at least 50% in a period of time of less than three months at a temperature at ambient temperature if a polymer is denoted biodegradable. However, there is no fixed definition for the term biodegradable in this regard.

The phase segregated block copolymers in accordance with the present invention preferably are shape memory polymers (hereinafter referred to as SMP). Shape memory is the ability of a material to remember its original shape, which phenomenon is based on a structural phase transformation and reflects the temperature activated strain recovery of polymers.

SMP are generally characterized as phase segregated, mostly linear, block copolymers having a hard segment and a soft segment. In many cases the hard segment is typically crystalline, with a defined melting point, and the soft segment is typically amorphous, with a defined glass transition temperature rather than melting point. In other embodiments, the soft segment is crystalline and has a melting point rather than a glass transition temperature. The melting point or glass transition temperature of the soft segment is substantially lower than the melting point or glass transition temperature of the hard segment.

When a shape memory polymer is heated above the melting point or glass transition temperature of the hard segment, the material can be shaped. This original shape can then be memorized by cooling the shape-memory polymer below the melting point or glass transition temperature of the hard segment. When the shaped SMP is cooled below the melting point or glass transition temperature of the soft segment the shape is deformed, a new temporary shape is fixed. The original shape is then recovered by heating the material above the melting point or glass transition temperature of the soft segments but below the melting point or glass transition temperature of the hard segment. In another method for setting a temporary shape, the material is deformed at a temperature lower than the melting point or glass transition temperature of the soft segment, resulting in stress and strain being absorbed by the soft segment. When the material is thereafter heated above the melting point or glass transition temperature of the soft segment, but below the melting point or glass transition temperature of the hard segment, the stresses and strains are relieved and the material returns to its original shape. The recovery of the original shape, which is induced by an increase in temperature, is called the thermal shape memory effect. In the polymers of the invention, elastic PDMS soft segments recover the strain and the PHA hard segments control the recovery by means of physical crosslinking and glass transition temperature.

Shape memory behaviour is in particular important when the polymers in accordance with the present invention are used for biomedical engineering purposes. In these cases the shape memory behaviour should occur at or around the body temperature Polylactic acid (PLA) which is a polymer commonly used in biomedical engineering is rigid and brittle and because of crystallization and a glass transtion temperature above body temperature (around 60° C.) has a lack of shapeability. The polymers of the present invention solve this problem by introducing flexible properties through the polydialkylsiloxane block. PDMS, the most preferred PDAS in accordance with the present invention, has a glass transition temperature well below body temperature. By introducing the flexible PDAS, and preferably PDMS, segments, the glass transition temperature of the polymers can be finely tuned and thus designed to be at around body temperature which is desirable for biomedical engineering applications, which is the preferred use for the polymers of the present invention.

Overall, the phase segregated block copolymers in accordance with the present invention show a good balance of strength and ductility for biomedical applications.

A preferred use of the polymers of the present invention is the application as shape recovery polymer stents. Compared to classical metal based stents the polymers of the present invention offer a number of important benefits.

The exceptional flexibility of the material allows the vessels into which the stent is implanted to maintain their natural mechanical properties and movements.

In the preferred embodiment, where the polymers of the present invention are biodegradable, there is no surgery necessary to remove the stent after the desired dilatation of the vessel has been achieved and there is no risk of late thrombosis like in metal based drug eluting stents. Furthermore, there is no need for expensive blood thinning agents to remove the thrombosis risk. The natural vasomotion of the arteries may be recovered.

During the period of biodegradation a controlled release drug delivery may be used to bring the natural arteries properties back before the stent is entirely degraded and dissolved.

Due to the shape memory behaviour of the phase segregated block-copolymer in accordance with the present invention, the stent may be shaped in a form to facilitate introduction into the body (e.g. the volume may be reduced for introduction into the body). After it has been brought into place, the stent expands to its original shape thus providing the desired widening of the blocked vessel. If the glass transition temperature is around body temperature this is achieved without further treatment of the body. Stents of this type are also referred to as activatable expandable stents which are activated using the temperature trigger of the body temperature. The stent is deformed into an elongated form facilitating introduction into the vessel, which elongated form is stable at room temperature. Then it is introduced into the body in the elongated form and brought into place. Upon warming to body temperature, the shape memory behaviour comes into play and the stent returns to its original shape providing the desired widening of the plugged vessel.

Although the advantages of the block copolymers in accordance with the present invention have been described above for the use as stents, there are numerous other applications where the block copolymers may be advantageously used. Sutures, orthodontic materials, bone screws, nails, plates, catheters, tubes, films, orthopedic braces, splints, tape for preparing casts and scaffolds for tissue engineering may be mentioned in this regard.

The following examples show preferred embodiments of the present invention.

EXAMPLES 1-4

Pre-dried Poly(dimethylsiloxane), bis(hydroxyalkyl) terminated (Mw~8500 g/mol, Mn 5600 g/mol, PDI 1.5, purchased from Sigma Aldrich) and lactide (98%, Aldrich) were charged in a clean pre-dried three-neck round-bottom flask (equipped with overhead KPG stirrer, reflux condenser) and dried in vacuo for 1 h. The reactor was flushed with Argon as an inert gas and was connected to Argon balloon during the reaction. Dry toluene (dried by Na in Ar atmosphere) was added as solvent and the reaction mixture was heated to 90° C. (using a silicon oil bath with a magnetic stirrer). $Sn(Oct)_2$ catalyst (1-0.5 mol-% of lactide) dissolved in 5 mL dry toluene was added drop wised and the reaction mixture was stirred for 20 h at 90° C. (after addition of glycolide 15 h more).

10-20 mL dry toluene was added for high viscous solutions. The temperature was decreased to 70° C. and 1,6-hexamethylene diisocyanate (HDI), dissolved in 5 mL dry toluene was added drop wised. The mixture was stirred for 2.5 h at 70° C. The temperature was elevated to 90° C. and pre-dried 1,4-Butanediol (BD) chain extender was added. The mixture was stirred for 2 h at 90° C. Oil bath was removed and the mixture was stirred over night at room temperature.

Work-Up

The polymer solution was diluted with the reaction solvent if it is too viscous, coagulated in 500 mL cold Ethanol, washed with technical grade Ethanol (3 times, 500 mL) and finally dried under reduced pressure to yield constant weight.

The details of the experiments are shown in Table 1.

TABLE 1

|  | | PDMS Macro-initiator | Lactide or Glycolide | Solvent | $Sn(Oct)_2$ µL | µL | BD µL |
|---|---|---|---|---|---|---|---|
| Ex. 1 | PSLLU 1:1 | 7.4 g | 7.2 g L-Lactide | 20 mL Toluene | 323 | 424 | 117 |
| Ex. 2 | PSLLU 1:1.5 | 7.4 g | 10.8 g L-Lactide | 30 mL Toluene | 485 | 424 | 117 |
| Ex. 3 | PSLLU 1:2 | 7.4 g | 14.4 g L-Lactide | 40 mL Toluene | 646 | 424 | 117 |
| Ex. 4 | PSLGU 1:0.8:0.2 | 7.4 g | 5.76 g L-Lactide + 1.16 g Glycolide (after 20 h of reaction) | 20 mL Toluene 10 mL DMAc (by Glycolide addition) | 162 | 424 | 117 |

The molecular weight of the starting materials, the intermediate block polymers obtained before addition of the HDI and of the final products products as well as the polydispersity index are given in Table 2 was determined by GPC as described before. as can be seen the PDMS block had a Mw of 8500 g/mol, the PLA block of between 6900 and 9200 g/mol and the final products had molecular weights Mw of from 55900 to 79400 g/mol. A comparative product (Example 4) obtained from PDMS and HDI only (without lactide) had a Mw of 135 000 and a polydispersity index of 1.36.

TABLE 2

| Example | Mw | PDI | PDMS content wt % | PLA content Wt % |
|---|---|---|---|---|
| 1 intermediate | 15,500 | 1.33 | 49 | 49 |
| 1 final | 79,400 | 1.55 | 48 | 49 |
| 2 intermediate | 17,700 | 1.29 | 41 | 58 |
| 2 final | 55,900 | 1.36 | 40 | 59 |
| 3 intermediate | 17,200 | 1.08 | 34 | 64 |
| 3 final | 58,600 | 1.34 | 33 | 66 |

TABLE 2-continued

| Example | Mw | PDI | PDMS content wt % | PLA content Wt % |
|---|---|---|---|---|
| 4 intermediate | — | — | — | — |
| 4 final | 135,470 | 1.36 | 100 | 0 |

The products in accordance with the invention showed good thermal stability and mechanical properties and were melt processible. They had an excellent property spectrum for implementation in temperature triggered cardiovascular implants, in particular for the manufacture of shape recovery polymer stents activatable at the human body temperature.

The invention claimed is:

1. A product comprising a stent, a suture, an orthodontic material, a bone screw, a nail, a catheter, a tube, an orthopedic brace, a splint, or a scaffold for tissue engineering, the product further comprising a phase segregated block-copolymer comprising repeating structural elements represented by formula I

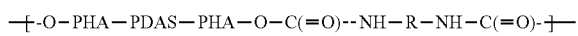

(I)

wherein PHA represents at least one block comprising one or more α-hydroxy acids, PDAS represents a central block comprising a dialkylsiloxane, the PDAS block has a weight average molecular weight in the range of from 4,000 to 10,000, the blocks PHA have a weight average molecular weight in the range of from 1,500 to 10,000, the phase segregated block copolymer has a weight average molecular weight of from 40,000 to 120,000, and R is a residue of a diisocyanate.

2. The product in accordance with claim 1 wherein the α-hydroxy acids are represented by the formula

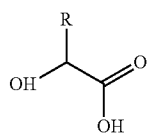

wherein R is a linear, branched, or cyclic aliphatic group having 1 to 30 carbon atoms, an aryl group comprising 6 to 30 carbon atoms which may comprise a fused ring, or an alkylaryl group having 7 to 40 carbon atoms.

3. The product in accordance with claim 1, wherein the α-hydroxy acid is selected from glycolic acid, lactic acid, malic acid, fumaric acid, citric acid, tartaric acid or from products obtained through diazotation of α-amino acids.

4. The product in accordance with claim 3 wherein the α-hydroxy acid is selected from malic acid, lactic acid or glycolic acid or mixtures thereof.

5. The product in accordance with claim 4 wherein the α-hydroxy acid is selected from lactic acid or glycolic acid or mixtures thereof.

6. The product in accordance with claim 1, wherein the alkyl groups of the dialkylsiloxane may be the same or different at each occurrence, and represent linear, branched or cyclic alkyl groups.

7. The product in accordance with claim 6 wherein the alkyl groups of the dialkylsiloxane are linear or branched alkyl groups having 1 to 12 carbon atoms.

8. The product of claim 7, wherein the phase segregated block-copolymer has a weight average molecular weight of from 50,000 to 90,000.

9. The product in accordance with claim 6 wherein the alkyl groups of the dialkylsiloxane are methyl groups.

10. The product of claim 9, wherein the phase segregated block-copolymer has a weight average molecular weight of from 50,000 to 90,000.

11. The product of claim 9, wherein the phase segregated block-copolymer has a weight average molecular weight of from 50,000 to 90,000, and wherein the copolymer is biodegradable.

12. The product of claim 9, wherein the phase segregated block-copolymer has a weight average molecular weight of from 50,000 to 90,000, wherein the copolymer is a shape memory copolymer.

13. The product of claim 6, wherein the phase segregated block-copolymer has a weight average molecular weight of from 50,000 to 90,000.

14. The product in accordance with claim 1, wherein the phase segregated block-copolymer is biodegradable.

15. The product in accordance with claim 1, wherein the phase segregated block-copolymer is a shape memory polymer.

16. The product in accordance with claim 1, wherein the product is a suture, an orthodontic material, a bone screw, a nail, a catheter, a tube, an orthopedic brace, a splint, or a scaffold for tissue engineering.

17. The product in accordance with claim 1, wherein the product is a shape recovery polymer stent.

18. The product of claim 1, wherein the phase segregated block-copolymer has a weight average molecular weight of from 50,000 to 90,000.

* * * * *